(12) United States Patent
Ye

(10) Patent No.: US 10,793,521 B2
(45) Date of Patent: Oct. 6, 2020

(54) CRYSTALLINE FORM II OF DEXTRAL OXIRACETAM, PREPARATION METHOD THEREFOR AND USE THEREOF

(71) Applicant: CHONGQING RUNZE PHARMACEUTICAL COMPANY LIMITED, Chongqing (CN)

(72) Inventor: Lei Ye, Chongqing (CN)

(73) Assignee: CHONGQING RUZER PHARMACEUTICAL COMPANY LIMITED, Chongqing (CN)

( * ) Notice: Subject to any disclaimer, the term of this patent is extended or adjusted under 35 U.S.C. 154(b) by 0 days.

(21) Appl. No.: 16/344,338

(22) PCT Filed: Jul. 7, 2017

(86) PCT No.: PCT/CN2017/092220
§ 371 (c)(1),
(2) Date: Apr. 23, 2019

(87) PCT Pub. No.: WO2018/076783
PCT Pub. Date: May 3, 2018

(65) Prior Publication Data
US 2019/0256464 A1    Aug. 22, 2019

(30) Foreign Application Priority Data

Oct. 24, 2016  (CN) .......................... 2016 1 0985131

(51) Int. Cl.
*C07D 207/273*    (2006.01)
*A61P 25/08*     (2006.01)
*A61K 31/4015*    (2006.01)

(52) U.S. Cl.
CPC ...... *C07D 207/273* (2013.01); *A61K 31/4015* (2013.01); *A61P 25/08* (2018.01); *C07B 2200/13* (2013.01)

(58) Field of Classification Search
CPC .............................. C07D 207/273; A61P 25/08
See application file for complete search history.

(56) References Cited

U.S. PATENT DOCUMENTS

| 4,124,594 | A | 11/1978 | Monguzzi | |
|---|---|---|---|---|
| 4,173,569 | A | 11/1979 | Banfi | |
| 9,126,928 | B2 * | 9/2015 | Ye | C07D 207/273 |
| 9,126,929 | B2 * | 9/2015 | Ye | C07D 207/273 |
| 9,238,622 | B2 * | 1/2016 | You | C07D 207/273 |
| 9,670,156 | B2 * | 6/2017 | Ye | A61K 31/4015 |
| 10,556,863 | B1 | 2/2020 | Ye | |
| 2019/0367454 | A1 | 12/2019 | Ye | |
| 2020/0071270 | A1 | 3/2020 | Ye | |

FOREIGN PATENT DOCUMENTS

| CN | 102249977 A | 11/2011 |
|---|---|---|
| CN | 102442936 A | 5/2012 |
| CN | 102600130 A | 7/2012 |
| CN | 102603607 A | 7/2012 |
| CN | 103553998 A | 2/2014 |
| CN | 105330582 A | 2/2016 |
| CN | 105820101 A | 8/2016 |
| CN | 106166150 A | 11/2016 |
| KR | 20060010000 | 2/2006 |
| WO | 2018076782 | 5/2018 |
| WO | 2018076783 | 5/2018 |
| WO | 2018076784 | 5/2018 |
| WO | 2018130063 | 7/2018 |

OTHER PUBLICATIONS

Almeida, J. et al., "New Enantioselective Synthesis of 4-Hydroxy-2-Oxypyrrolidine-N-Acetamide (Oxiracetam) from Malic Acid", Tethrahedron: Asymmetry, 3(11):1431-40, (1992).
Chen, X. et al., "Synthesis of (R) 4-Hydroxy-Oxo-1-Pyrrolidineacetamide", Fine Chemical Intermediates, 41(5):21-3, (2011).
International Application No. PCT/CN2017/092219; International Search Report (with translation) and Written Opinion of the International Searching Authority, dated Oct. 11, 2017; 9 pages.
International Application No. PCT/CN2017/092220; International Search Report (with translation) and Written Opinion of the International Searching Authority, dated Oct. 11, 2017; 8 pages.
International Application No. PCT/CN2017/092221; International Search Report (with translation) and Written Opinion of the International Searching Authority, dated Sep. 27, 2017; 16 pages.
International Application No. PCT/CN2017/118180; International Search Report (with translation) and Written Opinion of the International Searching Authority, dated Apr. 4, 2018; 12 pages.
Miyamoto, S., "Synthesis of 4-Hydroxy-2-Pyrrolidinone Derivatives", Neurosciences, 11:1-8, (1985).

(Continued)

*Primary Examiner* — Golam M Shameem
(74) *Attorney, Agent, or Firm* — Dennis A. Bennett; John Desper

(57) ABSTRACT

The present invention provides a crystalline form of dextral oxiracetam. The crystalline form has a diffraction peak when a diffraction angle, 2θ, is 17.76±0.2°, 20.16±0.2°, 21.20±0.2°, 24.17±0.2°, or 25.88±0.2°. The crystalline form of dextral oxiracetam can promote synthesis of phosphorylcholine and phosphoethanolamine, boosts cerebral metabolism, has a stimulating function on a specific central nervous pathway through a blood-brain barrier, and has special biological activity in the field of sedation and the antiepileptic field. The crystalline form of dextral oxiracetam of the present invention is a water-containing crystalline form, contains 0.5 water molecules, loses crystallization water at 73.5±2° C., and is melted and decomposed at 138.0±2° C. The crystalline form of dextral oxiracetam of the present invention can stably exist at room temperature and relative humidity of 0-95%, does not transform, is used for storage and formulation processing, and has low requirements for processing or storage humidity.

5 Claims, 1 Drawing Sheet

(56) References Cited

OTHER PUBLICATIONS

Byrn, S. et al., "Pharmaceutical Solids: A Strategic Approach to Regulatory Considerations", Pharmaceutical Research, 12(7):945-954, (1995).
Caira, M., "Cyrstalline Polymorphism of Organic Compounds", Topics in Current Chemistry, 198, 46 pages, (1998).
European Patent Application No. 17863355.8; Extended European Search Report; dated Feb. 24, 2020; 6 pages.
U.S. Appl. No. 16/344,340; Notice of Allowance, dated Dec. 11, 2019; 17 pages.

* cited by examiner

CRYSTALLINE FORM II OF DEXTRAL OXIRACETAM, PREPARATION METHOD THEREFOR AND USE THEREOF

This application is a national stage entry of PCT/CN2017/092220, filed Jul. 7, 2017, which claims priority to Chinese patent application no. 201610985131.9, filed Oct. 24, 2016, the disclosures of which are hereby incorporated by reference as if written herein in their entirety.

TECHNICAL FIELD

The invention relates to dextral oxiracetam, particularly to a crystalline form of dextral oxiracetam, preparation method and use thereof.

BACKGROUND ART

Oxiracetam, its CAS No. is 62613-82-5, is a new generation of drug for improving cerebral metabolism that was first synthesized in 1974 by SmithKline Beecham Corporation, Italy and has been available on the market in 1987. Oxiracetam is capable of promoting synthesis of phosphorylcholine and phosphoethanolamine, promoting cerebral metabolism, stimulating specific central nervous pathways through blood-brain barrier, and improving intelligence and memory. Studies have shown that its dextrorotatory form (dextral oxiracetam) has special biological activity in the field of sedation and anti-epilepsy, and has low toxicity and a broad range of pharmaceutical safety. Therefore, dextral oxiracetam is expected to become an alternative to the existing highly toxic anti-epileptic drugs.

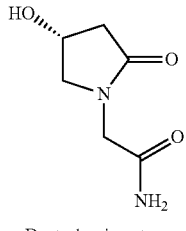

Dextral oxiracetam

In order to effectively develop dextral oxiracetam into pharmaceutical products, a solid form that is easy to manufacture and has acceptable chemical and physical stability is required to facilitate its processing and circulating storage. The crystalline solid form is generally superior to the amorphous form in terms of enhancing the purity and stability of the compound. At present, there are few studies on preparation methods and crystalline forms of dextral oxiracetam, and no crystalline form of dextral oxiracetam has been disclosed.

SUMMARY OF THE INVENTION

According to a first aspect of the invention, the invention provides a crystalline form of dextral oxiracetam, and the complete characteristics of the invention are described below, but for convenience, the provided crystalline form of dextral oxiracetam is referred to as "crystalline form II".

As set forth herein, all the parts are parts by weight, and all the percentages are mass percent, unless otherwise stated.

The object of the invention is achieved by:
a crystalline form II of dextral oxiracetam having diffraction peaks at diffraction angles 2θ of 17.76±0.2°, 20.16±0.2°, 21.20±0.2°, 24.17±0.2°, and 25.88±0.2°.

The crystalline form II of dextral oxiracetam described above has a relative peak intensity of 100% at the diffraction angle 2θ of 21.20±0.2°; a relative peak intensity of more than 70% and less than 100% at the diffraction angle 2θ of 20.16±0.2°; and relative peak intensities of not less than 40% at the diffraction angles 2θ of 17.76±0.2°, 24.17±0.2°, and 25.88±0.2°.

According to an embodiment of the invention, the crystalline form II of dextral oxiracetam described above has diffraction peaks at diffraction angles 2θ of 14.14±0.2°, 17.76±0.2°, 18.72±0.2°, 20.16±0.2°, 21.20±0.2°, 21.52±0.2°, 24.17±0.2°and 25.88±0.2°.

According to an embodiment of the invention, the crystalline form II of dextral oxiracetam described above has diffraction peaks at diffraction angles 2θ of 10.54±0.2°, 13.76±0.2°, 14.14±0.2°, 16.64±0.2°, 17.76±0.2°, 18.72±0.2°, 20.16±0.2°, 21.20±0.2°, 21.52±0.2°, 23.25±0.2°, 24.17±0.2°, 25.88±0.2°, 27.61±0.2°, 28.57±0.2°, 29.24±0.2° and 31.40±0.2°.

According to an embodiment of the invention, the crystalline form II of dextral oxiracetam described above is a water-containing crystalline form of dextral oxiracetam. Analysis of differential scanning calorimetry (DSC) shows that the crystalline form II of the dextral oxiracetam described above loses crystal water at 73.5±2° C., and melt and decomposed at 138.0±2° C. Specifically, the crystalline form II of the dextral oxiracetam described above has a differential scanning calorimetry (DSC) pattern as shown in FIG. 2.

According to a second aspect of the invention, the invention provides a method of preparing the crystalline form II of dextral oxiracetam, which has a simple process and is suitable for industrial production.

A method of preparing the crystalline form II of dextral oxiracetam comprises the following steps: dissolving dextral oxiracetam in a mixed solvent, filtering, sealing the filtrate with a lid, and stirring; filtering again, volatilizing the solvent from the filtrate in a desiccator to form crystals, collecting the crystals, and drying to obtain the crystalline form II of dextral oxiracetam. The mixed solvent is formed by mixing a good solvent and a poor solvent, wherein the good solvent is selected from DMF, dimethylacetamide, n-propanol or n-butanol, and the poor solvent is selected from dichloromethane, acetone, ethyl acetate, tetrahydrofuran, diethyl ether, n-hexane or petroleum ether; when the good solvent is DMF, the poor solvent is any one of dichloromethane, acetone, and ethyl acetate; when the good solvent is dimethylacetamide, the poor solvent is any one of tetrahydrofuran, acetone, and ethyl acetate; when the good solvent is n-propanol, the poor solvent is any one of tetrahydrofuran, diethyl ether, and n-hexane; and when the good solvent is n-butanol, the poor solvent is any one of dichloromethane, diethyl ether, and petroleum ether.

When the mixed solvent is a mixture of DMF (N, N-dimethylformamide) and any one of dichloromethane, acetone and ethyl acetate, it means that the mixed solvent can be a mixture of DMF and dichloromethane, or can be a mixture of DMF and acetone, or can be a mixture of DMF and ethyl acetate. Similarly, when n-propanol is mixed with any one of tetrahydrofuran, diethyl ether, and n-hexane, it means that the mixed solvent can be a mixture of n-propanol and tetrahydrofuran, or can be a mixture of n-propanol and diethyl ether, or can be a mixture of n-propanol and n-hexane; when dimethylacetamide is mixed with any one of tetrahydrofuran, acetone, and ethyl acetate, it means that the mixed solvent can be a mixture of dimethylacetamide and tetrahydrofuran, or can be a mixture of dimethylacetamide and acetone, or can be a mixture of dimethylacetamide and ethyl acetate; when n-butanol is mixed with any one of dichloromethane, diethyl ether and petroleum ether, it means that the mixed solvent can be a mixture of n-butanol and dichloromethane, or can be a mixture of n-butanol and diethyl ether, or can be a mixture of n-butanol and petroleum ether.

According to an embodiment of the invention, the mass-to-volume ratio (g/mL) of the dextral oxiracetam to the mixed solvent described above is from 1:2 to 1:10.

According to an embodiment of the invention, the volume ratio of the good solvent to the poor solvent in the mixed solvent described above is from 1:1 to 1:7; preferably from 1:2 to 1:5.

According to an embodiment of the invention, after the filtrate is sealed with the lid, the stirring time is from 3 h to 24 h, and the stirring speed is from 100 r/min to 150 r/min.

According to an embodiment of the invention, after the filtration and collection of crystals, the drying is performed at 10-40° C. and a relative humidity of 55-85% for 4-6 h; and preferably at 25-40° C. and a relative humidity of 65-85% for 5-6 h.

According to an embodiment of the invention, the method of preparing the crystalline form II of dextral oxiracetam described above comprises the following steps: dissolving dextral oxiracetam in a mixed solvent with a mass-to-volume ratio (g/mL) of the dextral oxiracetam to the mixed solvent of from 1:2 to 1:10, filtering, sealing the filtrate with a lid, and stirring at a speed of from 100 r/min to 150 r/min for 5-24 h; filtering again, leaving the filtrate in a desiccator to volatilize solvent in order to form crystals, collecting the crystals, and drying the collected crystals at 25-40° C. and a relative humidity of 65-85% for 5-6 h to obtain the crystalline form II of dextral oxiracetam. The mixed solvent is formed by mixing a good solvent and a poor solvent, and the volume ratio of the good solvent to the poor solvent is from 1:2 to 1:5, wherein the good solvent is selected from DMF, dimethylacetamide, n-propanol or n-butanol, and the poor solvent is selected from dichloromethane, acetone, ethyl acetate, tetrahydrofuran, diethyl ether, n-hexane or petroleum ether; when the good solvent is DMF, the poor solvent is any one of dichloromethane, acetone, and ethyl acetate; when the good solvent is dimethylacetamide, the poor solvent is any one of tetrahydrofuran, acetone, and ethyl acetate; when the good solvent is n-propanol, the poor solvent is any one of tetrahydrofuran, diethyl ether, and n-hexane; and when the good solvent is n-butanol, the poor solvent is any one of dichloromethane, diethyl ether, and petroleum ether.

The raw dextral oxiracetam of the invention can be a commercially available product or can be self-made, and the remaining raw materials or reagents are all commercially available products. In the preparation of the crystalline form of the invention, the filtration is a conventional solid-liquid separation method well known in the art.

According to a third aspect of the invention, the invention provides use of the crystalline form II of dextral oxiracetam (in a therapeutically effective amount) for the preparation of anti-epileptic drugs for preventing or treating epilepsy. The invention provides use of the crystalline form II of dextral oxiracetam for the preparation of anti-epileptic drugs for preventing or treating acute seizures of epilepsy, in particular for the preparation anti-epileptic drugs for preventing or treating acute and severe seizures of epilepsy. The invention provides use of the crystalline form II of dextral oxiracetam for the preparation of anti-epileptic drugs for preventing or treating generalized seizures of epilepsy. The invention provides use of the crystalline form II of dextral oxiracetam for the preparation of anti-epileptic drugs for preventing or treating partial seizures of epilepsy. The invention provides use of the crystalline form II of dextral oxiracetam for the preparation of anti-epileptic drugs for preventing or treating status epilepticus. The crystalline form II of dextral oxiracetam of the invention exhibits special pharmacological activities in stabilization of abnormal cerebral discharge, sedation, anti-epilepsy, and the like; and it has solubility of more than or equal to 100 mg/mL in water, and a high bioavailability.

According to a fourth aspect of the invention, the invention provides a pharmaceutical composition comprising the crystalline form II of dextral oxiracetam described above, and pharmaceutically acceptable excipients. The composition is in any clinically acceptable pharmaceutical dosage form, including tablets, powders, granules, injections, capsules, dripping pills, sustained release formulations, and lyophilized powders for injection for administrations including (but not limited to) oral, rectal, transvaginal, nasal, inhalation, topical (including transdermal) or parenteral administration.

ADVANTAGEOUS EFFECTS

The invention provides a crystalline form of dextral oxiracetam having diffraction peaks at diffraction angles $2\theta$ of 17.76±0.2°, 20.16±0.2°, 21.20±0.2°, 24.17±0.2°, and 25.88±0.2°, and having a relative peak intensity of 100% at the diffraction angle $2\theta$ of 21.20±0.2°; a relative peak intensity of more than 70% and less than 100% at the diffraction angle $2\theta$ of 20.16±0.2°; and relative peak intensities of not less than 40% at the diffraction angles $2\theta$ of 17.76±0.2°, 24.17±0.2°, and 25.88±0.2°. The crystalline form II of dextral oxiracetam of the invention is capable of promoting synthesis of phosphorylcholine and phosphoethanolamine, promoting cerebral metabolism, stimulating specific central nervous pathways through blood-brain barrier, and has special biological activity in the field of sedation, anti-epilepsy, and the like. The crystalline form II of dextral oxiracetam of the invention is a water-containing crystalline form, loses crystal water at 73.5±2° C., and melt and decomposed at 138.0±2° C. The crystalline form II of dextral oxiracetam of the invention has a high dissolution velocity in water, solubility of more than or equal to 100 mg/mL in water, and a high bioavailability. The crystalline form of the dextral oxiracetam of the invention is placed in a beaker, and subjected to an accelerated stability test in a constant temperature and humidity chamber at a temperature of 40° C.±2° C. and a relative humidity of 75%±5%. The results show that the crystalline form of the dextral oxiracetam of the invention did not undergo crystal transformation between 2 h and 15 d. The crystalline form of dextral oxiracetam of the invention can be stable and do not undergo crystal transformation at room temperature and a relative humidity of 0-95%. Also, it has good fluidity, the formulation process has high adaptability, and is suitable for producing a variety of pharmaceutical compositions, which can be made into pharmaceutical preparations such as tablets, capsules, dripping pills, sustained release formulations, and lyophilized powders for injection. The preparation method of the invention adopts cheap and easily available raw material, and the prepared crystalline form II of dextral oxiracetam has a high purity. The preparation method requires mild conditions and simple operations, introduces a low level of impurities and has a good reproducibility; the production process is easy to control, has a high safety and is suitable for industrial production.

DEFINITIONS

When describing the compound, crystalline form, uses, compositions and methods of the invention, the following terms have the following meanings, unless otherwise stated.

The term "therapeutically effective amount" means an amount that is sufficient to effect treatment when the amount is administered to a patient in need of treatment. As used herein, the term "treating" means treating a disease, illness or medical condition of a patient, for example, mammal (particularly human), comprising:

(a) preventing the occurrence of the disease, illness or medical condition, namely preventive treatment of the patient;

(b) improving the disease, illness or medical condition, namely eliminating or regressing the disease, illness or medical condition of the patient, including counteracting effects of other therapeutic agents;

(c) inhibiting the disease, illness or medical condition, namely mitigating or prohibiting the development of the disease, illness or medical condition of the patient; or (d) alleviating the symptoms of the disease, illness or medical condition of the patient.

It is noted that the singular form "a(n)", "one" and "the", as in the specification and the appended claims, can include plural referents, unless otherwise clearly stated in the content.

DETAILED DESCRIPTION OF THE PREFERRED EMBODIMENTS

The invention is described in detail by the following examples. It should be pointed out that the following examples are intended to further illustrate the invention, and are not to be construed as limiting the scope of the invention. Some non-essential modifications and adjustments to the invention can be made by those skilled in the art according to the aforementioned summary of the invention.

Preparation of Crystalline Form II of Dextral Oxiracetam

Example 1

1 g of dextral oxiracetam (Chongqing Runze Pharmaceutical Co., Ltd.) was dissolved in 6 mL of mixed solvent (2 mL of DMF and 4 mL of dichloromethane) solution, heated at 50° C. for dissolution, filtered, and the filtrate was sealed with a lid, stirred at a speed of from 100 r/min to 150 r/min for about 15 h, and filtered again. After filtering, the filtrate was left in a desiccator to volatilize solvent in order to form crystals. The crystals were collected, and dried at 30±2° C. and a relative humidity of 80-85% for 5-6 h, and obtained the crystals of dextral oxiracetam.

Example 2

The crystals of dextral oxiracetam obtained in Example 1 were subjected to a powder diffraction experiment.

Figure 1:
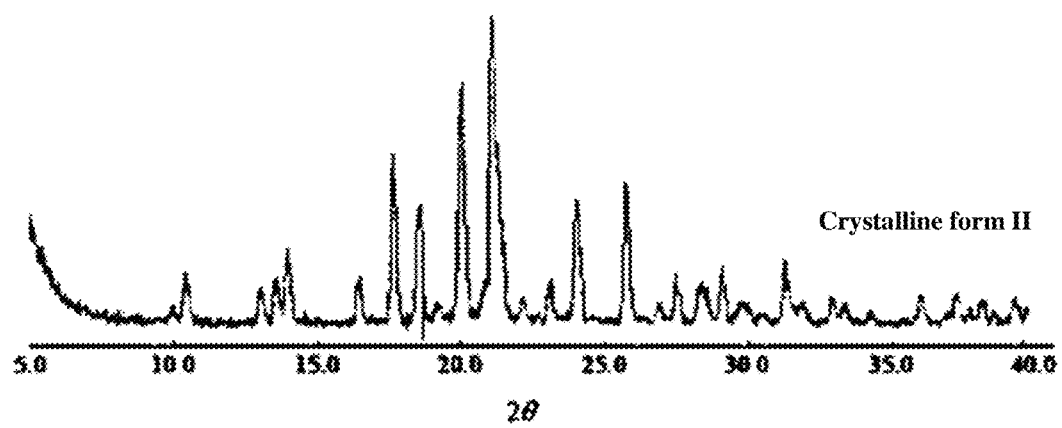
FIG. 1 is a powder diffraction pattern of the crystalline form II of dextral oxiracetam.

Powder Diffraction Measurement (XRPD):

Instrument and condition for measurement: the measurement was performed using the Bruker D2 PHASER powder diffractometer at room temperature. The measurement conditions were: Cu Kα (1.5418 Å) radiation as the light source, a voltage of 30 kV, a current of 10 mA, a test step length of 0.014°, a scanning rate of 0.1 s/step, and a scanning range of 5-40° (2θ). According to the measurement, the crystals of dextral oxiracetam prepared in Example 1 have diffraction peaks at diffraction angles 2θ of 10.54±0.2°, 13.76±0.2°, 14.14±0.2°, 16.64±0.2°, 17.76±0.2°, 18.72±0.2°, 20.16±0.2°, 21.20±0.2°, 21.52±0.2°, 23.25±0.2°, 24.17±0.2°, 25.88±0.2°, 27.61±0.2°, 28.57±0.2°, 29.24±0.2° and 31.40±0.2°. For convenience, the crystals are referred to as "crystalline form II of dextral oxiracetam", the powder diffraction pattern thereof is shown in FIG. 1, and the analysis of diffraction data is presented as Table 1 below.

TABLE 1

Powder diffraction peaks of crystalline form II
Crystalline form II of dextral oxiracetam

| Dihedral angle (°) | Intensity (I) |
|---|---|
| 10.131 | 6.9 |
| 10.540 | 16.5 |
| 13.152 | 10.9 |
| 13.768 | 14.4 |
| 14.141 | 24.3 |
| 16.641 | 15.2 |
| 17.764 | 55.6 |
| 18.721 | 38.1 |
| 19.388 | 4.8 |
| 20.166 | 77.6 |
| 21.205 | 100.0 |
| 21.527 | 35.9 |
| 22.307 | 7.2 |
| 23.250 | 13.3 |
| 24.176 | 40.0 |
| 25.882 | 46.9 |
| 27.129 | 6.3 |
| 27.617 | 16.1 |
| 28.575 | 13.0 |
| 29.242 | 17.4 |
| 31.403 | 20.6 |
| 32.082 | 7.2 |
| 33.088 | 8.1 |
| 33.530 | 6.7 |
| 36.190 | 10.2 |
| 37.425 | 8.5 |
| 38.288 | 7.4 |
| 38.708 | 3.9 |
| 39.440 | 7.4 |

As can be seen from Table 1 above, the crystalline form II of dextral oxiracetam of the invention has a relative peak intensity of 100% at the diffraction angle 2θ of 21.20±0.2°; a relative peak intensity of more than 70% and less than 100% at the diffraction angle 2θ of 20.16±0.2°; and relative peak intensities of not less than 40% at the diffraction angles 2θ of 17.76±0.2°, 24.17±0.2°, and 25.88±0.2°.

Figure 2:
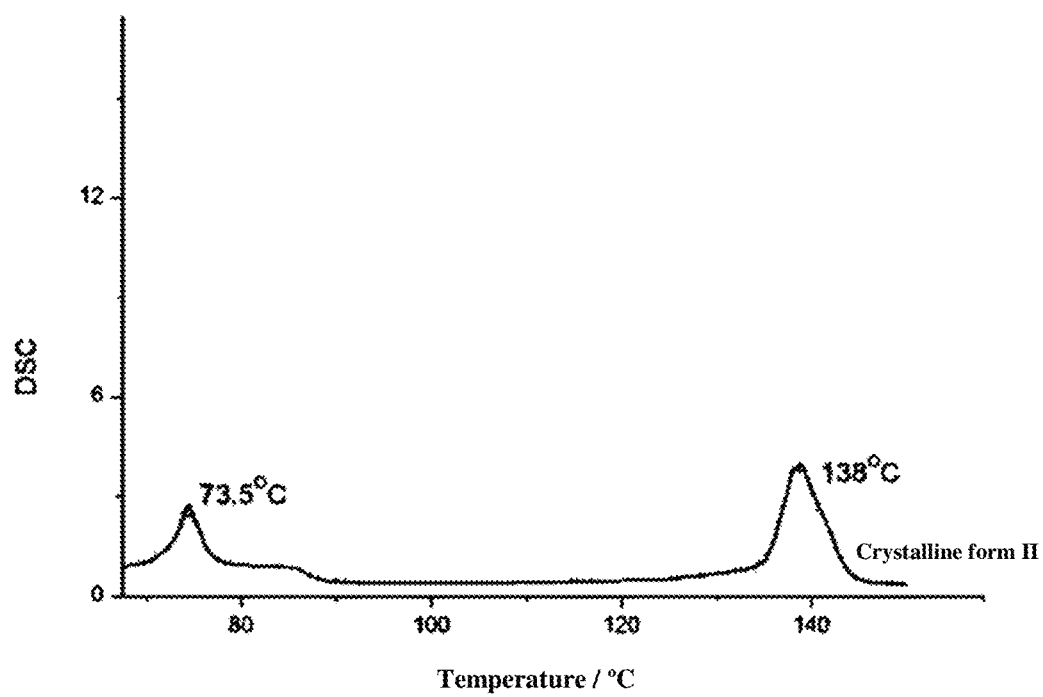
FIG. 2 is a differential scanning calorimetry (DSC) pattern of the crystalline form II of dextral oxiracetam.

Measurement of Differential Scanning Calorimetry (DSC) Pattern:

Instrument and condition for measurement: DSC test was carried out using a differential scanning calorimeter (STA 409PC, Netzsch, Germany). The test method comprises: accurately weighing an amount (1-2 mg) of the sample in a DSC crucible, sealing the crucible with a lid, heating the crucible and an empty crucible as a reference from 20° C. to 200° C., placing an aluminum crucible in a nitrogen atmosphere, and heating at a rate of 10° C./min, where the nitrogen flow rate in the sample chamber is 20 mL/min. The differential scanning calorimetry (DSC) pattern of the crystalline form II of dextral oxiracetam of the invention is shown in FIG. 2, the crystalline form II of dextral oxiracetam of the invention loses crystal water at about 73.5° C., and the endothermic transition temperature is about 138.0° C. The water content of the crystalline form II of dextral oxiracetam of the invention as measured by the Karl-Fischer method is 5.56% (theoretical water content: 5.52%), which indicates, in combination with thermogravimetric analysis characteristics, that the crystalline form II of dextral oxiracetam of the invention is a hemihydrate.

Referring to Example 1, the crystalline form II of dextral oxiracetam was prepared according to Examples 3-12.

Example 3

1 g of dextral oxiracetam was dissolved in 5 mL of mixed solvent (1 mL of DMF and 4 mL of ethyl acetate) solution, heated at 45° C. for dissolution, filtered, and the filtrate was sealed with a lid, stirred at a speed of about 150 r/min for about 12 h, and filtered again. After filtering, the filtrate was left in a desiccator to volatilize solvent in order to form crystals. The crystals were collected, and the collected crystals were dried at 30±2° C. and a relative humidity of 75-80% for 4-5 h. And the obtained crystals were identified as a crystal form II of dextral oxiracetam by using the method in Example 2.

Example 4

1 g of dextral oxiracetam was dissolved in 8 mL of mixed solvent (1 mL of DMF and 7 mL of acetone) solution, heated at 45° C. for dissolution, filtered, and the filtrate was sealed with a lid, stirred at a speed of about 100 r/min for about 20 h, and filtered again. After filtering, the filtrate was left in a desiccator to volatilize solvent in order to form crystals. The crystals were collected, and the collected crystals were dried at 25±2° C. and a relative humidity of 80-85% for about 6 h. And the obtained crystals were identified as a crystal form II of dextral oxiracetam by using the method in Example 2.

Example 5

500 mg of dextral oxiracetam was dissolved in 2 mL of mixed solvent (1 mL of n-propanol and 1 mL of tetrahydrofuran) solution, heated at 50° C. for dissolution, filtered, and the filtrate was sealed with a lid, stirred at a speed of about 120 r/min for about 8 h, and filtered again. After filtering, the filtrate was left in a desiccator to volatilize solvent in order to form crystals. The crystals were collected, and the collected crystals were dried at 15±2° C. and a relative humidity of 70-75% for about 10 h. And the obtained crystals were identified as a crystal form II of dextral oxiracetam by using the method in Example 2.

Example 6

1 g of dextral oxiracetam was dissolved in 6 mL of mixed solvent (1 mL of n-propanol and 5 mL of diethyl ether) solution, heated at 60° C. for dissolution, filtered, and the filtrate was sealed with a lid, stirred at a speed of about 150 r/min for about 5 h, and filtered again. After filtering, the filtrate was left in a desiccator to volatilize solvent in order to form crystals. The crystals were collected, and the collected crystals were dried at 40±2° C. and a relative humidity of 65-70% for about 4 h. And the obtained crystals were identified as a crystal form II of dextral oxiracetam by using the method in Example 2.

Example 7

1 g of dextral oxiracetam was dissolved in 6 mL of mixed solvent (1 mL of n-propanol and 5 mL of n-hexane) solution, heated at 30° C. for dissolution, filtered, and the filtrate was sealed with a lid, stirred at a speed of about 130 r/min for about 5 h, and filtered again. After filtering, the filtrate was left in a desiccator to volatilize solvent in order to form crystals. The crystals were collected, and the collected crystals were dried at 25±2° C. and a relative humidity of 85-95% for about 5 h. And the obtained crystals were identified as a crystal form II of dextral oxiracetam by using the method in Example 2.

Example 8

1 g of dextral oxiracetam was dissolved in 10 mL of mixed solvent (2 mL of n-butanol and 8 mL of dichloromethane) solution, heated at 40° C. for dissolution, filtered, and the filtrate was sealed with a lid, stirred at a speed of about 150 r/min for about 5 h, and filtered again. After filtering, the filtrate was left in a desiccator to volatilize solvent in order to form crystals. The crystals were collected, and the collected crystals were dried at 35±2° C. and a relative humidity of 80-85% for about 6 h. And the obtained crystals were identified as a crystal form II of dextral oxiracetam by using the method in Example 2.

Example 9

1 g of dextral oxiracetam was dissolved in 8 mL of mixed solvent (2 mL of dimethylacetamide and 6 mL of tetrahydrofuran) solution, heated at 30° C. for dissolution, filtered, and the filtrate was sealed with a lid, stirred at a speed of about 200 r/min for about 5 h, and filtered again. After filtering, the filtrate was left in a desiccator to volatilize solvent in order to form crystals. The crystals were collected, and the collected crystals were dried at 30±2° C. and a relative humidity of 80-85% for about 5 h. And the obtained crystals, which were identified as a crystal form II of dextral oxiracetam by using the method in Example 2.

Example 10

1 g of dextral oxiracetam was dissolved in 7 mL of mixed solvent (2 mL of dimethylacetamide and 5 mL of acetone) solution, heated at 30° C. for dissolution, filtered, and the filtrate was sealed with a lid, stirred at a speed of about 200 r/min for about 5 h, and filtered again. After filtering, the filtrate was left in a desiccator to volatilize solvent in order to form crystals. The crystals were collected, and the collected crystals were dried at 35±2° C. and a relative humidity of 75-80% for about 5 h. And the obtained crystals were identified as a crystal form II of dextral oxiracetam by using the method in Example 2.

Example 11

1 g of dextral oxiracetam was dissolved in 10 mL of mixed solvent (2 mL of dimethylacetamide and 8 mL of ethyl acetate) solution, heated at 30° C. for dissolution, filtered, and the filtrate was sealed with a lid, stirred at a speed of about 130 r/min for about 5 h, and filtered again. After filtering, the filtrate was left in a desiccator to volatilize solvent in order to form crystals. The crystals were collected, and the collected crystals were dried at 35±2° C. and a relative humidity of 75-80% for about 5 h. And the obtained crystals, which were identified as a crystal form II of dextral oxiracetam by using the method in Example 2.

Example 12

1 g of dextral oxiracetam was dissolved in 6 mL of mixed solvent (2 mL of n-propanol and 4 mL of n-hexane) solution, heated at 40° C. for dissolution, filtered, and the filtrate was sealed with a lid, stirred at a speed of about 150 r/min for about 4 h, and filtered again. After filtering, the filtrate was left in a desiccator to volatilize solvent in order to form crystals. The crystals were collected, and the collected crystals were dried at 25±2° C. and a relative humidity of 80-85% for about 5 h. And the obtained crystals were identified as a crystal form II of dextral oxiracetam by using the method in Example 2.

Performance Measurement Experiments of Crystalline Form II of Dextral Oxiracetam Example 13 Dynamic Vapor Sorption (DVS) Test The test parameters were given as follows: weighing: Ultra Digital Microbalance SMS Ultra Balance™; flow rate: $N_2$, 200 sccm, System Control Software: DVS-Intrinsic control software ver. 1.0.3.1, Data Analysis Software: Isotherm (ISO) analysis suite.

22.4 mg of sample of crystalline form II of dextral oxiracetam was weighed for the test, dried at RH=0%, the mass was balanced to ensure removal of moisture adsorbed on the surface, then placed on metal sample tray, and dried at 0% RH for 2 h. The test was performed at a constant temperature of 25° C., and the relative humidity (RH %) was controlled to vary cyclically from 0% to 90% to 0% RH with a 10% gradient. The variation of the sample weight with humidity was measured, which was combined with powder X-ray diffraction characterization to observe the effect of humidity on crystalline form transformation of the sample. The crystalline form of the sample was found to be still the crystalline form II of dextral oxiracetam.

Example 14 Accelerated Test

The accelerated test for crystalline form stability was performed in accordance with the provisions relating to the accelerated test of active pharmaceutical ingredients under "Guidelines for the Stability Test of Active Ingredient Pharmaceutical Ingredients and Pharmaceutical Preparations" of Pharmacopoeia 2010 Appendix XIXC. The crystalline form II of dextral oxiracetam was placed in a beaker and the test was carried out in a constant temperature and humidity chamber at a temperature of 40° C.±2° C. and a relative humidity of 75%±5%.

Test results: it was found that, after 2 h, there was no change in crystalline form II of dextral oxiracetam; after 10 days, there was no change in crystalline form II of dextral oxiracetam; and after 15 days, there was still no change in crystalline form II of dextral oxiracetam.

It can be seen that the crystalline form II of dextral oxiracetam of the invention can be stably present at room temperature and a relative humidity of 0-95%, and no crystal transformation occurs. When the crystalline form II of dextral oxiracetam of the invention is used for storage or formulation processing, the requirements on processing and storage humidity are reduced.

Preparation of compositions comprising crystalline form II of dextral oxiracetam Example 15

1000 capsules comprising crystalline form II of dextral oxiracetam were taken as examples, which were prepared by using 180 mg/capsule of the crystalline form II of dextral oxiracetam prepared by the method in Example 1, 90.8 mg/capsule of microcrystalline cellulose, 82 mg/capsule of compressible starch, 7.2 mg/capsule of talcum powder and an appropriate amount of 10% polyvinylpyrrolidone. The specific preparation method was given as follows: the raw materials and excipients were firstly passed through an 80-mesh sieve; the above-mentioned amounts of crystalline form II of dextral oxiracetam, microcrystalline cellulose and compressible starch were weighed and mixed uniformly, and 10% PVP ethanol solution was added to produce a soft material, pelletized, dried and granulated; the above-mentioned amount of talcum powder was added to the granules, mixed uniformly and filled into the capsules.

Example 16

60 g of the crystalline form II of dextral oxiracetam prepared by the method in Example 1 and 140 g of sorbitol were dissolved in 500 ml of water for injection in a mixing equipment under controlling the temperature between 50° C. and 58° C., and stirred until completely dissolved. The solution was cooled to 25° C. The activated carbon was added into the above prepared solution for decolorization, and then the activated carbon was removed by filtration. Phosphate buffer was added to adjust pH of the solution to 6.0, followed by adding water for injection to 5000 ml, filling and sealing, and sterilizing at 105° C. for 30 min, and obtained an injection.

The invention claimed is:

1. A crystalline form II of dextral oxiracetam having diffraction peaks at diffraction angles 2θ of 14.14±0.2°, 17.76±0.2°, 18.72±0.2°, 20.16±0.2°, 21.20±0.2°, 21.52±0.2°, 24.17±0.2° and 25.88±0.2°.

2. The crystalline form II of dextral oxiracetam according to claim 1, wherein the crystalline form II of dextral oxiracetam has a relative peak intensity of 100% at the diffraction angle 2θ of 21.20±0.2°; a relative peak intensity of more than 70% and less than 100% at the diffraction angle 2θ of 20.16±0.2°; and relative peak intensities of not less than 40% at the diffraction angles 2θ of 17.76±0.2°, 24.17±0.2°, and 25.88±0.2°.

3. The crystalline form II of dextral oxiracetam according to claim 1, wherein the crystalline form II of dextral oxiracetam has diffraction peaks at diffraction angles 2θ of 10.54±0.2°, 13.76±0.2°, 14.14±0.2°, 16.64±0.2°, 17.76±0.2°, 18.72±0.2°, 20.16±0.2°, 21.20±0.2°, 21.52±0.2°, 23.25±0.2°, 24.17±0.2°, 25.88±0.2°, 27.61±0.2°, 28.57±0.2°, 29.24±0.2° and 31.40±0.2°.

4. The crystalline form II of dextral oxiracetam according to claim 1, wherein the crystalline form II of dextral oxiracetam is melt and decomposed at 138.0±2° C.

5. The crystalline form II of dextral oxiracetam according to claim 1, wherein the crystalline form II of dextral oxiracetam has a differential scanning calorimetry (DSC) pattern as shown in FIG. 2.

* * * * *